United States Patent [19]

Nakao et al.

[11] Patent Number: 4,758,519
[45] Date of Patent: Jul. 19, 1988

[54] METHOD FOR CONTINUOUSLY ANALYSING TOTAL GASEOUS MERCURY

[75] Inventors: Shozo Nakao, Kiyose; Ichiro Matsuda, Osaka, both of Japan

[73] Assignee: Environmental Technical Laboratory, Ltd., Tokyo, Japan

[21] Appl. No.: 764,749

[22] Filed: Aug. 12, 1985

[30] Foreign Application Priority Data

Aug. 20, 1984 [JP] Japan .................. 59-172791

[51] Int. Cl.⁴ ..................... G01N 31/10; G01N 33/20
[52] U.S. Cl. ..................... 436/81; 436/147; 422/83
[58] Field of Search ............ 436/73, 81, 147; 422/62, 83, 78; 423/210 M

[56] References Cited

U.S. PATENT DOCUMENTS

| | | |
|---|---|---|
| 3,640,624 | 2/1972 | Anderson et al. |
| 3,704,097 | 11/1972 | Capuano .......... 436/81 X |
| 3,711,248 | 1/1973 | Coffey ............. 436/81 X |
| 3,844,719 | 10/1974 | Hammitt .......... 422/78 X |
| 3,852,604 | 12/1974 | Grengg ............ 436/81 X |
| 3,884,639 | 5/1975 | Sugiyama ............ 436/81 |
| 3,888,124 | 6/1975 | Campbell et al. ..... 55/72 X |
| 3,933,431 | 1/1976 | Trujillo et al. ...... 422/88 X |
| 4,023,929 | 5/1977 | Becker et al. ......... 436/81 |
| 4,080,169 | 3/1978 | Kloosterboer et al. |
| 4,138,215 | 2/1979 | Huber ............. 422/68 X |
| 4,206,183 | 6/1980 | Yamada et al. ..... 423/210 M |

FOREIGN PATENT DOCUMENTS 103642  6/1983  Japan .................. 436/73

OTHER PUBLICATIONS

Flaschka, et. al., *Quantitative Analytical Chemistry*, Willard Grant Press, Boston, Mass., (1980), 2nd Ed., pp. 427–429.
ISA Transactions, vol. 13, No. 4, 1974, pp. 296–302, Hal B. Cooper, Jr., et al.: "Measurement of Mercury Vapor Concentrations in Urban Atmosphere".
Japanese Industrial Standard (JIS), K-0222-1981.
Kindai Kagaku, (Modern Chemistry), No. 155, p. 46, (Feb., 1984).

*Primary Examiner*—Michael S. Marcus
*Assistant Examiner*—Jill Johnston
*Attorney, Agent, or Firm*—Oblon, Fisher, Spivak, McClelland & Maier

[57] ABSTRACT

A method for continuously analysing total gaseous mercury in a mercury compound-containing gas, characterized in that the gas is treated with a reducing agent to reduce the mercury compound in the gas to metal mercury prior to the measurement of the total gaseous mercury.

6 Claims, 1 Drawing Sheet

METHOD FOR CONTINUOUSLY ANALYSING TOTAL GASEOUS MERCURY

The present invention relates to a method for continuously analysing total gaseous mercury in a mercury compound-containing gas generated by the treatment of sludges or wastes, by the refining or processing of metals, by the combustion of fuels, or by the production of industrial products or chemical agents.

Heretofore, for the analysis of gaseous mercury, it has been common to employ a method as prescribed in Japanese Industrial Standard (JIS) K-0222-1981.

Further, recently, there has been a certain attempt to develop a method for continuously analysing gaseous mercury. For instance, Kindai Kagaku (Modern Chemistry) No. 155, page 46 (February issue) 1984, discloses the outline of a method for the analysis of mercury in a waste gas from an incinerator at a refuse treatment plant.

The method of JIS K-0222-1981 comprises trapping the gaseous mercury in the waste gas in an absorbing solution (a solution comprising potassium permanganate and sulfuric acid) by suction for a predetermined period of time, bringing the absorbing solution back to a laboratory, driving off mercury from the absorbing liquid, and analysing the mercury by means of a flameless atomic absorption spectrophotometer.

The result obtained by this method, gives only an average concentration of mercury during the trapping period of time (usually from 10 to 30 minutes) of the test gas, but does not give the instantaneous value. Accordingly, this method is not suitable for a continous analysis of the mercury concentration in a mercury-containing gas for the study of the process for the production of various chemical agents, or for the study of factors attributable to the variation in the mercury concentration in the waste gas from e.g. a refuse treatment plant, or for the study of substances causing mercury pollution.

On the other hand, the method disclosed in Kindai Kagaku (Modern Chemistry) No. 155, page 46 (February issue) 1984, comprises removing the moisture from the waste gas from the incinerator at a refuse treatment plant, then heating the gas to a temperature of from 700° to 800° C. by a heating furnace, and introducing it to an analyser. As the analyser, a flameless atomic absorption spectrophotometer of a laboratory scale is used, and FIG. 2 illustrates this analytical system.

The present inventors studied this method for possible application to a continuous method for the analysis of total gaseous mercury, as follows. Namely, a waste gas from an incinerator at a refuse treatment plant, was subjected to air-cooling and liquid-cooling to remove the moisture, and then returned to a normal temperature to obtain a dried gas, which is then heated to a temperature of from 700° to 800° C. by a heating furnace, and then introduced to and analysed by a flameless atomic absorption spectrophotometer. As a result, it was found that about 85% by weight of the total mercury contained in the waste gas transferred to the drain, and only about 15% by weight of the total mercury remained in the normal temperature dried gas. Further, it was found that the mercury in the drain was in the form of a compound such as mercury chloride or mercury oxide, and the mercury in the normal temperature dried gas was in the form of metal mercury.

Thus, it was found that this method might be useful for continuous analysis of metal mercury in the mercury compound-containing gas, but was not suitable for a continuous method for the analysis of the total gaseous mercury.

The present inventors have conducted extensive researches to overcome the drawback of the above-mentioned analytical method, and have found that an effective continuous method for the analysis of total gaseous mercury in a mercury compound-containing gas can be established by preliminarily reducing the mercury compound in the gas to metal mercury. The present invention is based on this discovery.

Namely, the present invention provides a method for continuously analysing total gaseous mercury in a mercury compound-containing gas, characterized in that said gas is treated with a reducing agent to reduce the mercury compound in the gas to metal mercury prior to the measurement of the total gaseous mercury.

Now, the present invention will be described in detail with reference to the preferred embodiments.

In the accompanying drawings.

Figure 1:
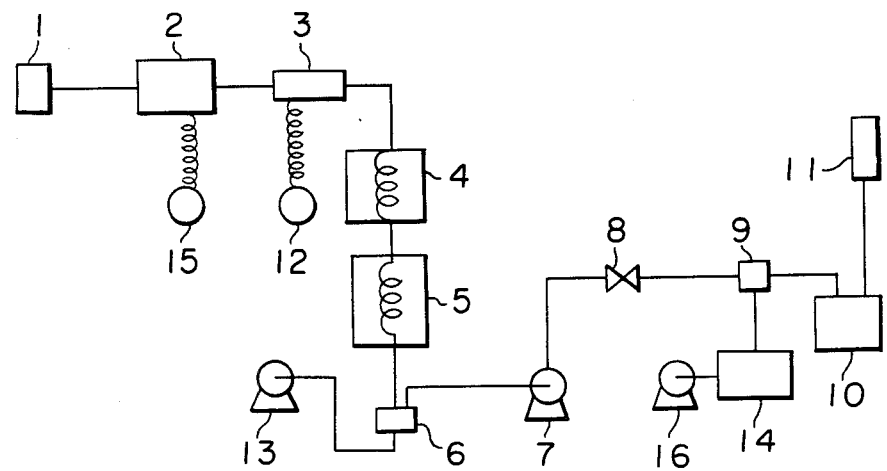
FIG. 1 is a schematic view illustrating an embodiment of the analytical system according to the present invention.

Referring to FIG. 1, reference numeral 1 designates a glass wool filter, numeral 2 designates a heating furnace, numeral 3 designates a reactor packed with a reducing agent, numeral 4 designates an air-cooler, numeral 5 designates a condenser, numeral 6 designates a gas-liquid separator, numeral 7 designates a suction pump, numeral 8 designates a needle valve to regulate the flow rate, numeral 9 designates a three-way valve, numeral 10 designates a flameless atomic absorption spectrophotometer for the analysis of mercury, numeral 11 designates a gas flow rate meter, numeral 12 designates a temperature controller, numeral 13 designates a drainage pump, numeral 14 designates a base line compensator, numeral 15 designates a temperature controller, and numeral 16 designates a suction pump.

Figure 2:
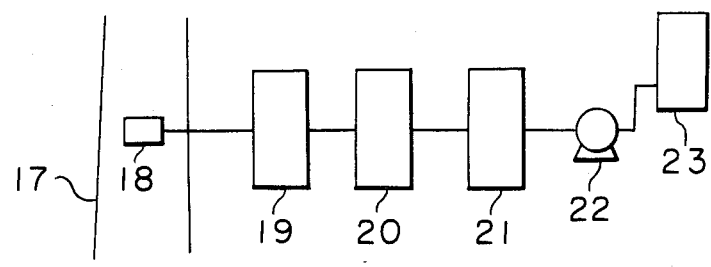
FIG. 2 illustrates the analytical system disclosed in Kindai Kagaku (Modern Chemistry) No. 155, page 46 (February issue) 1984.

Referring to FIG. 2, reference numeral 17 designates a chimney, numeral 18 designates a filter, numeral 19 designates a moisture remover, numeral 20 designates a heating furnace, numeral 21 designates a flameless atomic absorption spectrophotometer, numeral 22 designates a suction pump, and numeral 23 designates gas flow rate meter.

According to the present invention, the mercury compound-containing gas is taken out, for instance, through a filter, and optionally heated, and then the mercury compound in the gas is converted to metal mercury by means of a reducing agent, and the resulting metal mercury-containing gas comprising the converted metal mercury and the metal mercury originally contained in the starting gas, is cooled by a condenser to obtain a normal temperature dried gas, which is then introduced to a flameless atomic absorption spectrophotometer for the continuous analysis of the total mercury in the gas.

As the reducing agent, there may be employed any suitable reducing agent. The reducing agent preferably comprises a metal selected from the periodic table I group, II group and IV group, for instance, copper silver, gold, zinc, cadmium, lead and tin.

The temperature for the treatment of the mercury compound-containing gas varies depending upon the type of the reducing agent, and is preferably from 200° to 700° C. It is necessary to select the temperature so that the reducing agent will not form an amalgam with mercury.

It is preferred to heat the mercury-containing gas to a temperature of from 150° to 700° C. prior to the treatment with the reducing agent.

Hydrogen chloride, sulfur oxide, nitrogen oxide, carbon dioxide, etc. in the mercury compound-containing gas, do not substantially affect the method of the analysis according to the present invention.

FIG. 1 is a schematic view illustrating an embodiment of the analytical system according to the present invention.

The continuous method for the analysis according to the present invention will be described with reference to FIG. 1. The mercury compound-containing gas is passed through a silica wool filter 1 to remove dusts, etc., and, if necessary, heated by a heating furnace 2 equipped with a temperature controller 15, and then the gas is introduced to a reactor 3 packed with a reducing agent and controlled to a predetermined temperature, whereby the mercury compound in the mercury compound-containing gas is reduced to metal mercury. Then, the metal mercury-containing gas is cooled by an air cooler 4 and a condenser 5 to obtain a normal temperature dried gas, and the condensed product is separated by a gas-liquid separator 6 and discharged by a pump 13. The normal temperature metal mercury-containing dried gas is sucked by a suction pump 7, and the flow rate is adjusted by a needle valve 8. The normal temperature metal mercury-containing dried gas and air from a base line compensator 14, are alternately introduced at a definite interval into a flameless atomic absorption spectrophotometer 10 by the base line compensator 14 and a three-way valve 9. The air is supplied from a suction pump 16. The flow rates of the metal mercury-containing dried gas and the air from the base line compensator, are watched by the gas flow rate meter 11.

Now, the present invention will be described in further detail with reference to Examples. However, it should be understood that the present invention is by no means restricted to these specific Examples.

EXAMPLES

A waste gas from an incinerator having a temperature of from 200° to 250° C. at a refuse treatment plant, was analysed by the analytical system as shown in FIG. 1. The analytical conditions were as follows. As the reducing agent, 3 ml of metal tin having a grain diameter of about 3 mm was packed in a reactor of 8 mm in diameter×60 mm in length. The temperature of the heating furnace was controlled at a level of 600°±10° C., and the temperature of the reactor was controlled at a level of 200°±5° C. The metal mercury-containing gas was cooled to 10° C. by the air-cooler and the condenser. The flow rate as measured by the flow meter was controlled to be from 1 to 2 liter/min, and the continuous analysis was conducted by MAS-50 Model Flameless Atomic Absorption Spectrophotometer manufactured by Perkin-Elmer Corp. The results of the Examples of the present invention are shown in Table 1 together with the results of the Comparative Examples wherein the heating furnace and the metal tin-packed reactor were not used.

TABLE 1

| | Working conditions | | Result of the analysis* | |
|---|---|---|---|---|
| | Temperature of the heating furnace | Temperature of the reactor | Mercury contained in the dried gas | Mercury contained in the condensed water** |
| Example 1 | 600° C. | 200° C. | 180 | 0.5 |
| Example 2 | — | 200° C. | 171 | 14 |
| Comparative Example 1 | — | — | 25 | 163 |
| Comparative Example 2 | 600° C. | — | 30 | 145 |

*Unit: mg × $10^{-3}$/m$^3$
**Analysed in accordance with JIS K-0222-1981

Having thus described the present invention, it should be understood that according to the present invention, the analysis of total gaseous mercury can continuously be conducted, whereby reliable results are obtainable quickly.

As mentioned before with respect to the conventional analytical system, if the analysis is conducted without passing the mercury compound-containing gas through the reducing agent-packed reactor, only the metal mercury originally contained in the mercury compound-containing gas will be analysed. Accordingly, by the combination of this method with the method of the present invention, it is possible not only to measure the total mercury in the mercury compound-containing gas, but also to conduct separate quantitative analyses of the metal mercury and the mercury compound.

Needless to say, the present invention may be applicable, not only to the waste gas from an incinerator at the refuse treatment plant as in the Examples, but also to the continuous analysis of total gaseous mercury generated by the refining or processing of metals, the combustion of fuels, the production of industrial products or chemical agents, or the like.

We claim:

1. A method for continuously analyzing total gaseous mercury in a mercury compound-containing gas which comprises:
    (i) treating said mercury compound-containing gas which treating step consists essentially of contacting said mercury compound-containing gas with a reducing agent at a temperature of from 200° C.-700° C. to convert mercury compounds in said mercury compound-containing gas to metal mercury;
    (ii) cooling the gas resulting from said treating step which gas comprises said metal mercury converted from said mercury compounds and metal mercury originally present in said mercury compound-containing gas,
    (iii) condensing and removing moisture from the gas resulting from said cooling step to obtain a dried gas, and
    (iv) supplying said dried gas to a mercury analyzer for continuous analysis of the total gaseous mercury in said dried gas,
    wherein said reducing agent is an elemental metal selected from the group consisting of metals in groups I, II and IV of the Periodic Table.

2. The method according to claim 1, wherein said reducing agent is tin metal.

3. The method according to claim 1, wherein said reducing agent is zinc metal.

4. The method according to claim 1, wherein said mercury analyzer is a flameless atomic absorption spectrophotometer.

5. The method according to claim 1, wherein said mercury compound-containing gas is heated prior to said treating step.

6. The method according to claim 5, wherein said mercury compound-containing gas is heated to a temperature of from 150° C.–700° C. prior to said treating step.

* * * * *